United States Patent
Heinonen

(12) 
(10) Patent No.: US 6,474,333 B1
(45) Date of Patent: Nov. 5, 2002

(54) METHOD FOR PURGING A MEDICAL FLUID ADMINISTRATION SYSTEM

(75) Inventor: Erkki Heinonen, Helsinki (FI)

(73) Assignee: Instrumentarium Corp., Helsinki (FI)

( * ) Notice: Subject to any disclaimer, the term of this patent is extended or adjusted under 35 U.S.C. 154(b) by 3 days.

(21) Appl. No.: 09/593,902

(22) Filed: Jun. 14, 2000

(51) Int. Cl.[7] .................. A61M 15/00; A61M 16/00
(52) U.S. Cl. .................. 128/203.12; 128/204.18; 128/204.23; 128/204.26
(58) Field of Search .............. 128/203.12, 203.18, 128/204.18, 204.23, 204.26

(56) References Cited

U.S. PATENT DOCUMENTS

| | | | | |
|---|---|---|---|---|
| 5,558,083 A | * | 9/1996 | Bathe et al. | 128/203.12 |
| 5,871,009 A | * | 2/1999 | Rydgren et al. | 128/203.12 |
| 6,089,229 A | * | 7/2000 | Bathe et al. | 128/204.21 |
| 6,125,846 A | * | 10/2000 | Bathe et al. | 128/202.22 |
| 6,131,571 A | * | 10/2000 | Lampotang et al. | 128/204.21 |
| 6,158,434 A | * | 12/2000 | Lugtigheid et al. | 128/204.22 |
| 6,164,276 A | * | 12/2000 | Bathe et al. | 128/202.22 |

FOREIGN PATENT DOCUMENTS

| | | |
|---|---|---|
| EP | 879612 | 11/1998 |
| EP | 0 937 479 A2 | 8/1999 |

* cited by examiner

Primary Examiner—Aaron J. Lewis
Assistant Examiner—Darwin P. Erezo
(74) Attorney, Agent, or Firm—Andrus, Sceales, Starke & Sawall, LLP

(57) ABSTRACT

A method for purging an undesired fluid, such as $NO_2$, from a fluid gas administration system, such as an NO gas administration system. In normal operation, the system supplies NO to the patient with the breathing gases inspired during the inspiration phase of the respiratory cycle. Breathing gases are expired during the expiration phase of the respiratory cycle. In the method, the expiration phase of the patient's respiratory cycle is sensed and the administration system is operated in the expiration phase to pass NO through the system to flush out the system, including any $NO_2$ present, into the expired breathing gases of the patient. Since the contents of the system are discharged during the expiration phase, the $NO_2$ gas so removed is carried away from the patient with the expired breathing gases. The purging of the system is typically carried out at startup of the system and during an expiration phase prior to administering NO during the inspiration phases of the patient's respiratory cycle for medicinal purposes. The method may be used with administration systems for other types of fluids, such as diagnostic gases and nebulized liquids.

26 Claims, 2 Drawing Sheets

METHOD FOR PURGING A MEDICAL FLUID ADMINISTRATION SYSTEM

BACKGROUND OF THE INVENTION

The present invention relates to a method for purging a medical fluid gas administration system of undesired fluids. The invention may find use in a variety of applications such as purging a therapeutic nitric oxide (NO) gas administration system of nitrogen dioxide ($NO_2$) or purging a diagnostic sulfur hexafluoride ($SF_6$) administration system to ensure proper administration of such a gas to a patient.

In connection with the former application, is it now widely recognized that the administration of NO gas to a patient increases pulmonary capillary vasodilatation. The NO gas is administered by placing it in the breathing gases inhaled by the patient, typically in very small concentrations of, for example, 0.5 nanomoles to 5.0 micromoles of NO per breath. The increase in vasodilatation improves blood-gas exchange between breathing gases and the blood providing efficacious treatment for respiratory and other diseases. The NO gas is usually supplied from a high pressure cylinder through a pressure regulator to a gas administration system. The gas administration system establishes the NO dosage and supplies same for mixing with the breathing gases prior to, or during, inhalation. The NO so supplied may be mixed with the breathing gases to provide a generally constant concentration of NO in the inhaled breathing gases. Or, the NO may be A provided to the inhaled breathing gases as short pulse doses of gas, one of which is delivered in each inhalation, usually at the beginning of inhalation.

In many cases the administration of NO is carried out when the patient is on a respirator that assists or supplants the patients own breathing action.. The respirator is connected to the patient by a breathing circuit comprised of a inspiratory limb, a Y-piece connector, an expiratory limb, and a patient limb. The inspiratory limb extends from an inspiration outlet of the respirator to the Y-piece connector. The expiratory limb connects the Y-piece connector with the respirator expiration inlet. The patient limb connects the Y-piece connector to an endotracheal tube or a breathing mask forming a conduit from the Y-piece connector to the patient's airways and lungs. When a respirator is in use, the NO gas is delivered to the patient limb or inspiratory limb of the breathing circuit to be provided to the patient during the inspiratory phase of the patient's respiratory cycle.

In other cases, the NO gas is provided to a spontaneously breathing patient through a face mask or nasal appliance.

A problem in the administration of NO is that NO reacts with oxygen to form nitrogen dioxide ($NO_2$). Nitrogen dioxide is toxic even at very low concentrations and human exposure, for example in an occupational setting, is usually limited to 2–3 parts per million. For patients, who typically are already ill, there should be almost no exposure to $NO_2$. The amount of $NO_2$ formed during the reaction depends on the concentrations of oxygen and NO that are present and the time during which the two gases are in contact with each other.

In an NO gas administration system, $NO_2$ can form when air and NO are both present in the gas delivery conduits of the system. The presence of air can arise during the connection of the apparatus to the high pressure NO source cylinder and pressure regulator, through leakage or migration of air into the system during and between uses, due to gas diffusion through the materials of the system when in long term storage, and for other reasons. For example, when the cylinder pressure regulator is connected to the NO supply cylinder, the internal volume of the pressure regulator contains air at ambient pressure. On connection to the cylinder, this. air can diffuse backward into the cylinder, form $NO_2$, and contaminate the contents of the cylinder. Typical cylinder connection protocols thus call for purging of the pressure regulator and system immediately following connection of the system to the NO gas supply cylinder. While this may eliminate this source of $NO_2$, the causes noted above, and others, remain resulting in $NO_2$ being formed in the gas administration system.

Several approaches have been developed for purging NO gas administration systems prior to use to ensure that $NO_2$ is removed before the administration of NO to the patient begins. For example, U.S. Pat. No. 5,558,083 and European Patent Publication No. 879,612 show the use of a purging valve for system purging purposes. To purge the system, the system is placed in operation to deliver NO gas from the supply source through the system. The purging valve is operated to connect the outlet of the administration system to a gas exhaust rather than to the breathing circuit or other means for delivering NO to the patient. The NO gas moving through the system flushes the $NO_2$ out of the system and into a gas scavenger or the ambient environment. After the purging has been completed, the purging valve is operated to reconnect the outlet of the system to the breathing circuit or other means to deliver NO gas to the patient. The European patent publication further shows the use of the NO delivery control valve in the system for purging purposes rather than a separate purging valve dedicated to purging purposes. The delivery control valve is operated either automatically or through a prompt device alerting the user to purge the delivery system when the administration of NO is commenced. Use of the NO delivery control valve for purging has the advantage of reducing the number of components needed in the NO gas administration system. A disadvantage in utilizing the same control valve and pathway for purging as for delivery is that the patient must be instructed not to use the device until after the purging is complete.

European Patent Publication No. 937479 shows purging of an NO gas administration system if the NO delivery is not triggered by the patient's breathing within a predetermined time. This prevents the formation of $NO_2$ in the delivery device from the migration of ambient air into the system.

Sulfur hexafluoride ($SF_6$) is used to determine the functional residual capacity of a patient's lungs and for other pulmonary diagnostic purposes. Small, precisely determined amounts of such an indicator gas are entrained in the inhaled breathing gases to the patient. The amount of indicator gas exhaled by the patient is measured and the exhaled and inhaled gas measurements used in computational techniques that provide the desired diagnostic information. Purging of the delivery line for the indicator gas assists in accurately administering the indicator gas since with purging the gas content of the delivery line is known.

In other cases, it is desired to administer drugs by placing them in the inhaled breathing gases of a patient. Commonly such drugs are in liquid form and are atomized to a fine mist by a nebulizer as they are placed in the inhaled breathing gas. When the drug is to be changed, it is desirable to purge the supply line from the drug reservoir to the nebulizer to ensure the drugs are not mixed.

BRIEF SUMMARY OF THE INVENTION

The present invention provides a technique for purging a fluid administration system of undesired fluids, in a manner that both avoids the need for additional components, such as purging valves, and eliminates the possibility of the patient inhaling the purged fluids. The present invention lends itself to automatic purging of the system on startup and/or before administration of breathing gases to the patient without the need for patient intervention.

In the technique of the present invention, the expiration phase of the patient's respiratory cycle is sensed. A bidirectional sensor in the breathing gas flow path of the patient may be used to sense the direction of gas flow, and hence the expiration phase of the respiratory cycle. The fluid administration system is operated during the expiration phase to pass the administered fluid through the system for discharge at its outlet. The administered fluid moving through and out of the system carries with it any undesired fluids in the system. However, since the discharge occurs during expiration, the fluids, including the undesired fluids, so removed and discharged from the system to the breathing gases are carried away from the patient with the expired breathing gases. The discharged gases thus do not reach the patient. Once the purging of the system is completed, the supply of fluid during the expiratory phase stops and the normal administration of fluid from the fluid administration system during the inspiratory phase may commence.

To ensure that no fluid discharged during purging reaches the patient, it is preferable that the purging operation be carried out in the initial portion of the expiratory phase of the respiratory cycle. The administered fluid used in purging may be provided as a pulse of fluid in one or more expiratory phases of the patient's respiratory cycles.

When a respirator is in use with the patient, the outlet of the administration system may be connected to the patient limb of the breathing circuit. The fluid administration system may also be connected to the Y-piece connector of the breathing circuit. Or, the system may be connected to the inspiratory limb of the breathing circuit. A bypass flow from the inspiratory limb to the expiratory limb in the expiratory phase of the respiratory cycle carries off the fluids discharged during purging of the system. The gas flow sensor used to detect the phases of respiratory cycle is typically placed in the breathing circuit. Or, the inspiratory and expiratory phases of the respiratory cycle can be determined from the respirator. The determination of the phases of the respiratory cycle is usually already carried out in fluid administration systems since it is needed for sensing the inspiratory phases in which the administered fluid is supplied to the patient.

The invention can also be utilized when the patient is spontaneously breathing, i.e. without a respirator, with the use of a means to detect the inspiration and expiration phases of the respiratory cycles of the spontaneously breathing patient.

It is preferable that the volume of gas passed through the gas administration system be sufficient to ensure that all undesired fluid is removed from the system. When the administered fluid is a gas, the purging volume needed is determined by the gas volume within the administration system in accordance with the internal volume of the system and prevailing gas pressures. Due to internal gas mixing, the purge volume should be larger than the internal gas volume and preferably at least twice the internal gas volume.

Various other features, objects, and advantages of the invention will be made apparent from the following detailed description and the drawings.

DETAILED DESCRIPTION OF THE PREFERRED EMBODIMENT

Figure 1:
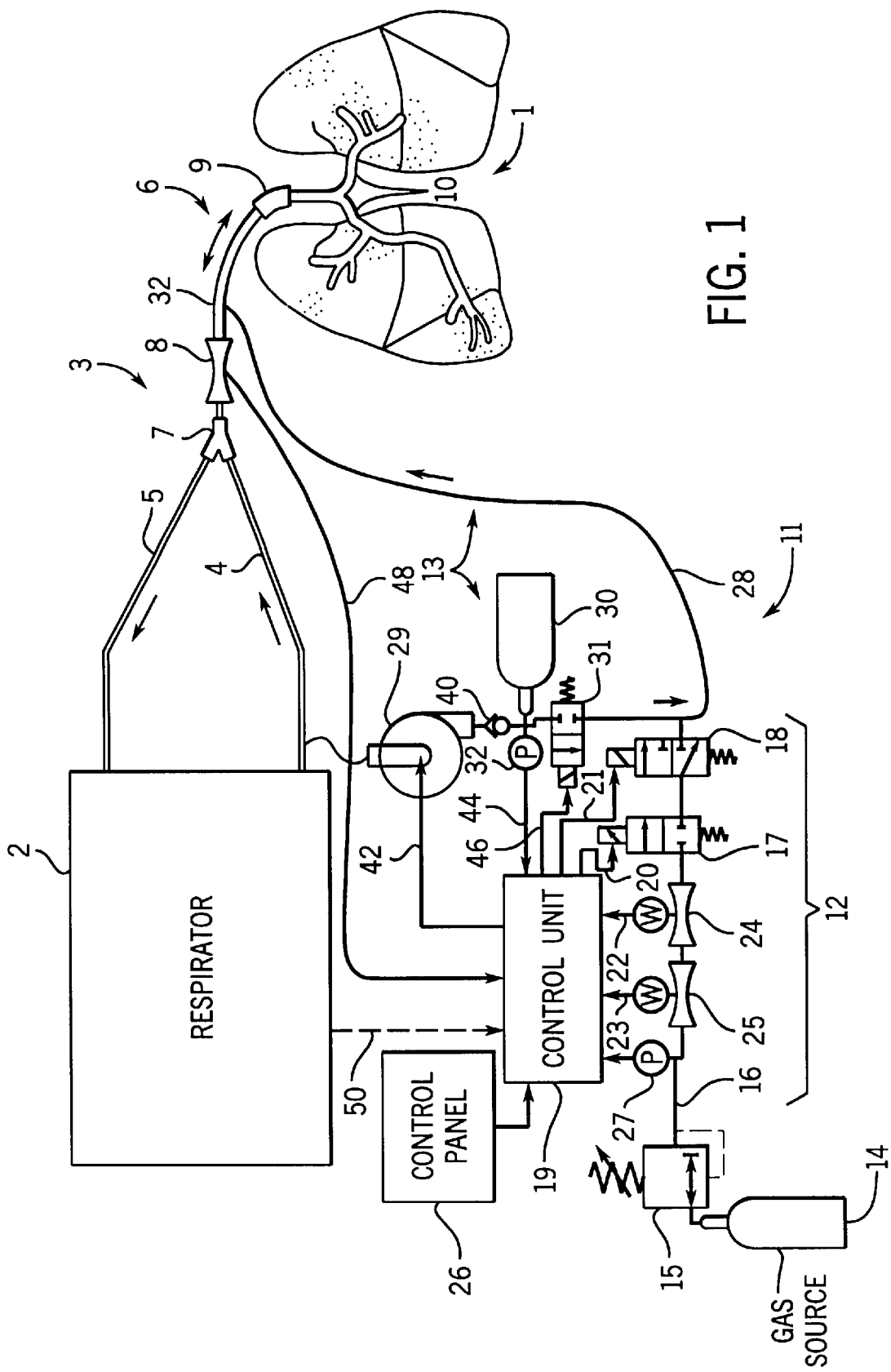
FIG. 1 shows a fluid administration system with which the present invention may be practiced.

As shown in FIG. 1, the present invention may be practiced in an arrangement in which breathing gases for a patient are supplied and removed from the lungs 1 of the patient by a respirator 2. Respirator 2 may be of conventional construction and is connected to the lungs 1 of the patient by a breathing circuit 3. Breathing circuit 3 comprises inspiratory limb 4, Y-piece connector 7, expiratory limb 5, and patient limb 6. The inspiratory limb 4 extends from the inspiration outlet of respirator 2 to Y-piece connector 7. The expiratory limb 5 connects the Y-piece connector 7 with the respirator expiration inlet. Patient limb 6 connects Y-piece connector 7 with an endotracheal tube 9 or a breathing mask that forms a breathing passage from the Y-piece connector into the airways 10 of the patient and further into lungs 1. Patient limb 6 may include a flow sensing element 8. The breathing circuit may also contain other components for monitoring and therapeutic purposes, such as a humidifier or filter, depending on the needs of the patient.

FIG. 1 also shows a fluid administration system with which the method of the present invention may be practiced. Fluid administration system 11 comprises flow metering portion 12 and gas transport portion 13. The nitric oxide administration system is shown separate from respirator 2 in FIG. 1, but the two elements could be integrated together, if desired. The invention is described, below in conjunction with an administration system for a therapeutic gas, such as NO. As noted, above, it may also be used in conjunction with other types of drug administration systems or with an administration system for a diagnostic gas, such as $SF_6$.

The flow metering portion 12 of NO administration system 11 includes delivery line 16 for the NO gas. The inlet of line 16 connects with supply cylinder 14 in which the NO gas is stored under pressure, typically a pressure of up to 20 MPa. Supply pressure regulator 15 at cylinder 14 or in line 16 reduces the high pressure gas in supply cylinder 14 to an appropriate level for metering, e.g. 50–300 kPa. Other suitable NO gas supplies, such as a hospital supply manifold, may be used with system 11, if desired. To monitor the existence and amount of the gas pressure in line 16, pressure sensor 27 is coupled to line 16.

Line 16 includes series connected flow metering valve 17 and pulse control valve 18 which are operated by control unit 19, via control lines 20 and 21, respectively, to provide pulse doses of NO gas. Control unit 19 receives inputs from flow sensing element 8 in patient limb 6 and pressure sensor 27, as well as from redundant flow sensors 24 and 25 connected in line 16 that measure the amount of gas moving through line 16. Sensors 24 and 25 provide inputs to control unit 19 in conductors 22 and 23, respectively. Control unit 19 is also connected with control panel 26 for providing NO dose related parameters to control unit 19 and optionally also for presenting information on the operation of the administration system. Control unit 19 operates valves 17 and 18, through control lines 20 and 21, to provide pulse doses of NO gas corresponding to the dose related parameters set in control panel 26.

The output of delivery line 16 is connected to NO gas transport line 28 of gas transport portion 13 of NO administration system 11. In the embodiment of the invention shown in FIG. 1, transport line 28 is connected to patient limb 6 at junction 32 to deliver the NO gas to lungs 1 of the patient during inspiration by the patient.

Gas transport portion 13 of NO administration system 11 includes pump 29, the inlet of which is connected to inspiration limb 4 of breathing circuit 3. The output of pump 29 is connected to transport gas reservoir 30 via check valve 40. Pump 29 is operated by control unit 19 through conductor 42. The pressure in transport gas reservoir is measured by pressure sensor 32 and provided to control unit 19 in conductor 44. The pressure loading and gas release of transport gas reservoir 30 is controlled by valve 31, operated by control unit 19 via control line 46.

An advantage obtained through the use of NO administration system 11 of the type shown in FIG. 1 is the ability to deliver precisely timed, small pulses of nitric oxide gas to the patient through use of the metering valve 17 and pulse control valve 18 while at the same time allowing the system to be positioned away from the crowded working environment near the patient, for example at patient limb 6, the pulses of NO gas being supplied to the breathing circuit along gas transport line 28.

In the normal operation of system 11, to administer NO to the patient during inspiration, the user can define, through control panel 26, NO gas dosing related parameters, such as the dose volume to be delivered per inspiration, the starting point of a pulse dose within the inspiration phase of the respiratory cycle of the patient, the end point of the pulse dose, or alternatively the duration of dose supply, etc. From the information control unit 19 obtains from control panel 26, control unit 19 determines the operating conditions for the NO administration system, opens metering valve 17 and pulse control valve 18 to form pulse doses of NO for delivery to the breathing gases, and monitors the delivered pulse volume with flow sensors 24 and 25. Synchronously with the dose formation in metering portion 12, control unit 19 operates valve 31 to provide a carrier gas flow in conduit 28 to transport the pulse doses of NO gas to junction 32 and into patient limb 6 during inspiration by the patient for supply to the lungs I of the patient along with the inspired breathing gases. Control unit 19 also receives the signal from patient limb flow sensing element 8 in conductor 48 for use in coordinating the delivery of NO pulses with the respiratory cycles of the patient so that the pulses are delivered to the breathing gases during the inspiration phase. This may be accomplished by determining that the gas flow direction in patient limb 6 is toward the patient.

Prior to the normal operation of system 11 in supplying therapeutic doses of NO to the patient, purging of the system is in order to avoid subjecting the patient to $NO_2$. As noted above, the $NO_2$ results from the reaction of the NO gas with oxygen. The source of oxygen is ordinarily the breathing gases for the patient which may comprise air or other oxygen containing gas mixture. The formation of $NO_2$ may occur in connection of the NO supply cylinder to the system, at startup when NO contacts the ambient air or other breathing gases present in the system, and between uses when air migrates into the system to contact NO remaining in the system from an earlier use.

In accordance with the present invention, purging of the system is carried out in the following manner. To purge system 11, the system is operated to pass a quantity of NO gas through metering portion 12 and transport portion 13 during the expiration phase of the respiratory cycle. The NO gas, which may be provided as a pulse of gas, flushes the existing contents, including any $NO_2$ present in delivery line 16 and transport line 28, out of the lines to patient limb 6. However, since the patient is expiring, the gases so supplied move away from the lungs 1 of the patient through patient limb 6, Y-piece connector 7, exhalation limb 5, and respirator 2 and are not supplied to the patient. The patient is thus not exposed to any $NO_2$.

Figure 2A:
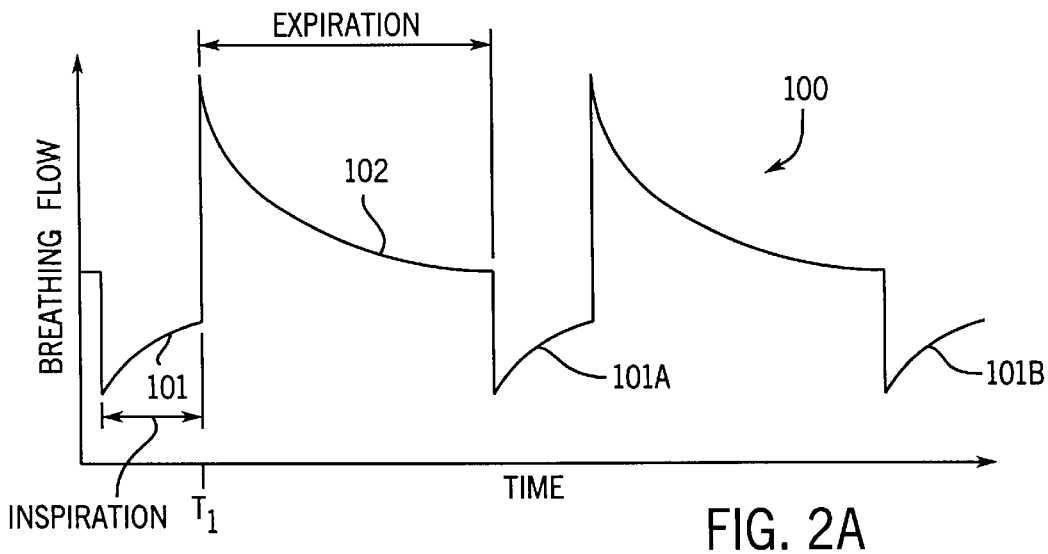
FIGS. 2A and 2B are graphs showing the manner in which the present invention is practiced.
Figure 2B:
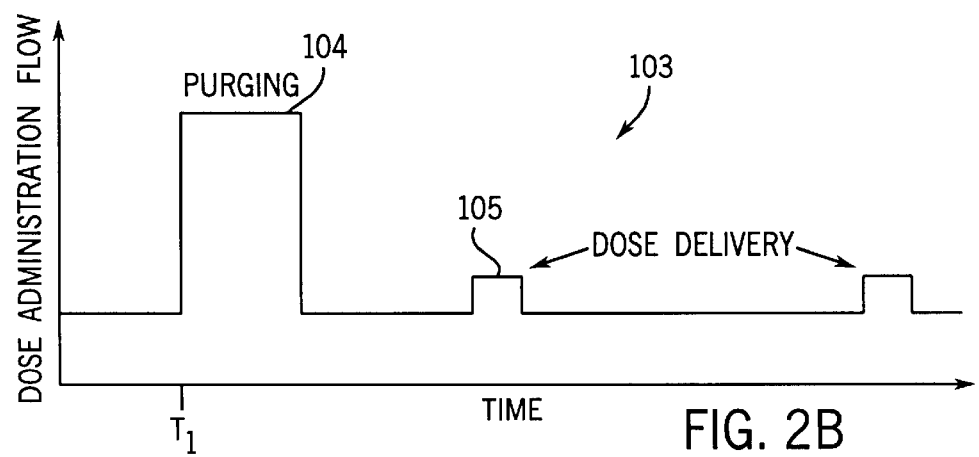

FIGS. 2A and 2B graphically shows the manner in which the purging of NO administration system 11 according to the invention may be carried out. Curve 100 shows a typical patient breathing flow pattern as sensed by gas flow sensor 8 in patient limb 6 and provided to control unit 19 in control line 48. In the inspiration phase 101, breathing gases pass from inspiration limb 4 through Y-piece connector 7 and patient limb 6 in a flow direction from respirator 2 to lungs 1 of the patient. During the expiration phase 102, the flow direction is reversed as breathing gases flow from lungs 1 of the patient through patient limb 6, Y-piece connector 7 to expiration limb 5 and to respirator 2. The opposite flow directions are shown by the opposite extensions of graphs 101 and 102 from the horizontal reference line shown at the left hand side of FIG. 2A.

To purge the system, when the direction of breathing gas flow sensed by flow sensor 8 indicates that expiration has commenced, as at $T_1$ in FIG. 2A, control unit 19 operates valves 17, 18 and 31 to pass the purging gas through lines 16 and 28 to junction 32 in patient limb 6. This is shown as purging pulse 104 in FIG. 2B. The graph 104 may represent the signal provided by sensors 24 and 25 in line 16 and show the supply and passage of a pulse of gas.

This operation would typically be carried out in an expiration phase of the respiratory cycle that follows startup of the NO administration system and is prior to any supply of NO during the inspiratory phases of the respiratory cycle to the patient for therapeutic purposes. This later administration is shown as NO pulse doses 105 in inspiration phases 101A and 101B with the NO pulse doses being delivered at the beginning of the inspiratory phase to ensure they are drawn into the lungs of the patient. It is deemed preferable to initiate the purging gas flow immediately following initiation of the expiration phase as shown in FIG. 2B as this will ensure that the purged gases will be carried away from the patient to the fullest extent possible in the expired breathing gases.

The volume of purging gas needed to flush out the system depends on the internal dimensions and pressure of the system. To ensure adequate purging of the system, the purging gas volume should be larger than the internal volume of the system and preferably at least twice the internal volume. In a typical embodiment of an administration system operating at a pressure of 100 kPa, the internal gas volume may amount to 10 ml and the purging volume may be 20 ml. If a purged volume of this magnitude is discharged into ambient air, it does not cause a contamination risk due to the small purged volume. For example, discharging a purged volume of 20 ml into a cubic meter of air would typically result in a $NO/NO_2$ concentration of only 20 parts per billion (ppb) which is well below any hazardous level.

While FIG. 2B shows the purging volume 104 delivered during a single expiration phase, a succession of smaller purging volumes in the expiration phases of successive respiratory cycles may be used, if desired, or if required because of high internal volume or performance limitations of system 11 on the size of NO dose that can be delivered.

The amount of purging gas employed, the number of pulses used, and the timing of the pulses are controlled by control unit 19.

Also, while the above description describes the use of patient gas flow sensing element 8 to indicate the initiation of the expiration phase for use in triggering the purging operation, other sources of sensing the inspiration phase-expiration phase of the respiratory cycle may be used. For example, respirator 2 typically generates this information in the course of its normal operation. A signal identifying the expiratory phase of the respiratory cycle may be provided to control unit 19 by respirator 2 through control line 50, as shown in dotted lines in FIG. 1.

After the NO administration system 11 has been adequately purged, the nitric oxide administration can be started for a subsequent inspiration phase as shown by NO pulse 105 in FIG. 2.

Further, while the invention has been described in connection with the pulse administration of NO gas, it will be appreciated that it can be used with other NO gas flow patterns, it being only necessary that the NO purging gas volume be entrained in expired breathing gases of the patient to carry the purged gases away from the patient. Such other flow patterns can include constant NO concentration delivery. Also, while NO administration junction 32 has been shown as located in patient limb 6, it can also be provided in Y-piece connector 7 or in inspiratory limb 4, near Y-piece connector 7 if there is a bypass flow of breathing gases directly from the inspiratory limb to the expiratory limb during expiration for passing the purging gas during expiration to expiratory limb 5 for removal from the breathing circuit and the patient.

While the invention has been described in conjunction with the use of a respirator 2, it will be appreciated that it may also be used with spontaneously breathing patients when a means for identifying the expiration phase of the respiratory cycle, such as a flow or pressure sensor in a face mask worn by the patient, is present.

A diagnostic gas administration system with which the present invention may be utilized may be of the type shown in applicant's U.S. patent application, Appln. Ser. No. 09/082,110, filed May 20, 1998 now U.S. Pat. No. 6,131,572, issued Oct. 17, 2000, which is incorporated herein by reference. A drug administration system of the nebulizer type with which the present invention may be utilized may be of the type shown in applicant's U.S. patent application, Appln. Ser. No. 09/397,529, filed Sep. 16, 1999, which is incorporated herein by reference.

It is recognized that other equivalents, alternatives, and modifications in addition to those expressly stated, are possible and within the scope of the appended claims.

What is claimed is:

1. A method for purging undesired fluid from a fluid administration system, the fluid administration system having a normal operating mode in which a fluid administered by the system is passed through the system from a source to breathing gases inspired by the patient during an inspiration phase of the respiratory cycle of the patient, the respiratory cycle of the patient having an expiration phase in which breathing gases are expired by the patient, said method comprising the steps of:

sensing a state of a patient's respiratory cycle;

operating the fluid administration system to pass administered fluid through the system to remove undesired fluid from the fluid administration system, the operation of the fluid administration system being carried out responsive to the respiratory cycle sensing in a discrete interval within a respiratory cycle of the patient that results in the removed, undesired fluid being subsequently carried away from the patient with expired breathing gases of the patient; and supplying undesired fluid removed from the system by the passage of the administered fluid to the breathing gases of the patient.

2. A method according to claim 1 further defined as operating the fluid administration system to pass a volume of fluid through the system sufficient to remove the undesired fluid from the system.

3. A method according to claim 2 further defined as passing a predetermined volume of fluid through the fluid administration system.

4. A method according to claim 3 wherein the fluid administration system has internal dimensions and pressure and wherein the method is further defined as passing a volume of fluid through the fluid administration system in accordance with at least one of the internal dimensions and pressure of the fluid administration system.

5. The method according to claim 3 wherein the administration fluid system is further defined as one for administering gaseous fluid and wherein the system has an internal gas volume, and wherein the method is further defined as passing a volume of administered fluid gaseous fluid greater than the internal gas volume of the administration system through the system.

6. A method according to claim 5 further defined as passing a volume of gaseous fluid at least twice as large as the internal gas volume of the fluid administration system through the system.

7. A method according to claim 1 further defined as operating the fluid administration system during the expiratory phase of the patient's respiratory cycle prior to supplying administered fluid to the patient during the inspiratory phases of the patient's respiratory cycle.

8. A method according to claim 1 wherein undesired fluid is present in the fluid administration system prior to startup of the system and wherein the steps of the method are carried out at the startup of the fluid administration system.

9. A method according to claim 8 wherein the steps of the method are automatically carried out at the startup of the fluid administration system.

10. A method according to claim 1 wherein the fluid administration system is coupled to a breathing circuit connecting the patient to a respirator, wherein the breathing circuit has a patient limb for the patient, and wherein the method is further defined as supplying the fluid removed from the system to the expired breathing gases of the patient in the patient limb of the breathing circuit.

11. A method according to claim 1 wherein the fluid administration system is coupled to a breathing circuit connecting the patient to a respirator, wherein the breathing circuit has a Y connector for the patient and wherein the method is further defined as supplying the fluid removed from the system to the expired breathing gases of the patient in the Y connector of the breathing circuit.

12. A method according to claim 1 wherein the fluid administration system is coupled to a breathing circuit connecting the patient to a respirator, wherein the breathing circuit has an inspiration limb for the patient and wherein the method is further defined as supplying the fluid removed from the system to the breathing gases in the inspiration limb of the breathing circuit and bypassing the removed fluid to an expiration limb of the breathing circuit.

13. A method according to claim 1 includes the further step of operating the fluid administration system in the normal operating mode following purging of the system.

14. A method according to claim 1 further defined as sensing the expiration phase of a patient's respiratory cycle and as operating the fluid administration system during the expiratory phase of the patient's respiratory cycle.

15. A method according to claim 1 or 14 further defined as operating the fluid administration system to pass a pulse of fluid through the system.

16. A method according to claim 15 further defined as providing the pulse of fluid at the beginning of the expiration phase of the patient's respiratory cycle.

17. A method according to claim 15 further defined as passing the pulse of fluid through the system during a single expiratory phase.

18. A method according to claim 15 further defined as passing the pulse of fluid through the system in each of a plurality of expiratory phases of respiratory cycles.

19. A method according to claim 14 further defined as sensing an expiration phase of the respiratory cycle from a flow direction of the patient's breathing gases.

20. A method according to claim 19 further defined as sensing the flow direction of the patient's breathing gases with a gas flow sensor.

21. A method according to claim 19 wherein the fluid administration system is coupled to a breathing circuit connecting the patient to a respirator and wherein the sensing step is further defined as using an indication from the respirator to sense an expiration phase of the patient's respiratory cycle.

22. A method according to claims 1, 3, 15, 16, 20, 10, 11 or 14 wherein the fluid administration system is an NO gas administration system and wherein he step of operating the gas administration system is further defined as passing NO gas through the system to flush the system of undesired gases.

23. A method according to claims 1, 3, 15, 16, 20, 10, 11, or 14 wherein the fluid administration system is a diagnostic gas administration system and wherein the step of operating the gas administration system is further defined as passing diagnostic gas through the system to flush the system of undesired gases.

24. A method according to claims 1, 3, 15, 16, 20, 10, 11, or 14 wherein the fluid administration system is a nebulized drug administration system and wherein the step of operating the drug administration system is further defined as passing nebulized drug through the system to flush the system of undesired fluid.

25. A method according to claim 14 wherein the administration system is further defined as one for administering gaseous fluids and where the operating step is further defined as operating the fluid administration system to pass administered gaseous fluid through the system.

26. A method for purging undesired gas from an NO gas administration system, the administration system having a normal operating mode in which NO gas is passed through the system from a gas source to the breathing gases inspired by a patient during an inspiration phase of the respiratory cycle of the patient, the respiratory cycle of the patient having an expiration phase in which breathing gases are expired by the patient, the NO gas administration system having an internal gas volume, said method comprising the steps of:

sensing the expiration phase of a patient's respiratory cycle;

operating the NO gas administration system during the expiration phase to pass at least one pulse of NO gas through the system to flush the system of undesired gas, a volume of the pulse or pulses being greater than the internal gas volume of the system; and supplying gases removed from the system by the passage of the NO gas to the breathing gases of the patient for being carried away from the patient with expired breathing gases of the patient.

* * * * *